United States Patent [19]

McCarthy et al.

[11] 4,262,005
[45] Apr. 14, 1981

[54] COMPOUNDS, COMPOSITIONS AND METHODS FOR CONTROLLING PESTS

[75] Inventors: John F. McCarthy, Nottingham; Bryan H. Palmer, Burton Joyce; Thomas I. Watkins, Nottingham, all of England

[73] Assignee: The Boots Company Limited, Nottingham, England

[21] Appl. No.: 966,790

[22] Filed: Dec. 6, 1978

Related U.S. Application Data

[63] Continuation-in-part of Ser. No. 859,089, Dec. 9, 1977, abandoned.

[30] Foreign Application Priority Data

May 31, 1978 [GB] United Kingdom ............... 25633/78

[51] Int. Cl.³ ............................................. A01N 43/50
[52] U.S. Cl. ................................. 424/273 R; 548/315
[58] Field of Search ...................... 424/273; 548/315

[56] References Cited

U.S. PATENT DOCUMENTS

| | | | |
|---|---|---|---|
| 3,190,802 | 6/1965 | Zeile et al. | 548/315 |
| 3,462,433 | 8/1969 | Stahle et al. | 548/315 |
| 3,752,810 | 8/1973 | Stahle et al. | 548/315 |
| 3,804,833 | 4/1974 | Stahle et al. | 548/315 |
| 3,988,345 | 10/1976 | Franzmair | 548/315 |

FOREIGN PATENT DOCUMENTS

741947 5/1970 Belgium .................................. 548/315

OTHER PUBLICATIONS

Van Hoeven et al–J. of Med. Chem. vol. 18 Jan.–Jun. 1975 pp. 90, 92–93, 98 & 99.

*Primary Examiner*—Allen J. Robinson
*Attorney, Agent, or Firm*—Gordon W. Hueschen

[57] ABSTRACT

A new method of controlling pests harmful to domestic animals and certain novel pesticidal compositions are described. Compounds for use in the method have the formula

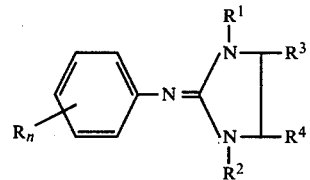

in which n is 0 to 5, R is halo, alkyl, trihaloalkyl, cyano alkoxy or alkoxycarbonyl, $R^1$ and $R^2$ are each hydrogen, alkyl alkenyl, alkynyl, acyl, or hydrocarbyloxycarbonyl and $R^3$ and $R^4$ are each hydrogen or alkyl; or an acid addition. The method is of particular value for controlling ectoparasites which attack cattle and pigs. Certain of the compounds are novel.

15 Claims, No Drawings

COMPOUNDS, COMPOSITIONS AND METHODS FOR CONTROLLING PESTS

This application is a continuation in a part application of Ser. No. 859,089 filed Dec. 9, 1977, now abandoned.

This invention relates to methods for controlling animal pests and to certain new compositions for use in pest control.

Pests that attack animals can cause a great deal of damage and result in considerable economic loss. A particularly harmful group of pests are those which attack the external parts of an animal and are known as ectoparasites. They cause severe irritation and can sometimes result in the mortality of domestic animals, a term which is used in this specification to mean (a) livestock namely pigs, Equidae such as horses and ruminants such as cattle, sheep and goats and (b) pets namely cats and dogs.

One aspect of the invention is a method for controlling pests harmful to domestic animals, which comprises applying to the locus of the pest a compound of the following formula

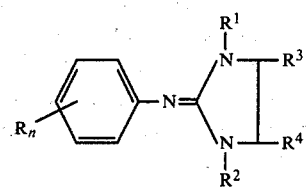
I in which n is 0 to 5, R is halo, alkyl, trihaloalkyl, cyano, alkoxy or alkoxycarbonyl, $R^1$ and $R^2$ are each hydrogen, alkyl, alkenyl, alkynyl or acyl, and $R^3$ and $R^4$ are each hydrogen or alkyl; or an acid addition salt thereof. The term "locus" is used to imply that the active compounds can be applied to the pest itself or to the habitat of the pest. For example it is sometimes convenient to spray the quarters in which an animal is kept in order to eliminate the pest from the animal's surroundings. More usually the animal is treated by external application of the active compound either as a precaution against pest attack or in order to combat an infestation of pests.

It is known that imidazolidine compounds of the type I, above, in which either $R^1$ or $R^2$ is hydrogen and in which both $R^1$ and $R^2$ are hydrogen, may exhibit tautomerism between the iminoimidazolidine form (formula I) and its aminoimidazoline tautomer. For convenience throughout this specification all compounds are referred to as iminoimidazolidines.

In formula I, n can be 0 to 5, more usually 0 to 3. There is preferably at least one substituent and n is often 2. If n is more than one, the values of R need not be identical so that there can be mixed substituents on the phenyl ring.

When R is halo it can be iodo, chloro, fluoro or bromo and is preferably chloro or bromo. When it is alkyl R is preferably a group containing from 1 to 4 carbon atoms, such as for example methyl, ethyl, propyl, or butyl, especially methyl. In the case when R is trihaloalkyl it is preferably trifluoromethyl and when R is alkoxy the substituent is preferably one containing 1 to 4 carbon atoms, especially methoxy. When R is alkoxycarbonyl the substituent preferably contains 2 or 3 carbon atoms and is methoxycarbonyl or ethoxycarbonyl. In an especially preferred instance there are two substituents on the phenyl ring which are in the 2- and 4-positions.

The groups $R^1$ and $R^2$ can be the same or different and when they are alkyl they preferably contain up to ten carbon atoms such as an alkyl group containing 1 to 4 carbon atoms, for example, methyl, ethyl, propyl and butyl. When $R^1$ and $R^2$ is alkenyl it preferably contains 2 to 5 carbon atoms and examples are the allyl and methylallyl radicals. When $R^1$ or $R^2$ is alkynyl it preferably contains 2 to 5 carbon atoms such as for example prop-2-ynyl.

When $R^1$ or $R^2$ is acyl it can be any convenient acyl group of the formula $R^5CO$. The radical $R^5$ can be, for example, (a) an alkyl group preferably containing up to ten carbon atoms, especially from 1 to 5 carbon atoms, (b) a cycloalkyl group preferably containing 3 to 7 carbon atoms, (c) an alkoxyalkyl group preferably containing 2 to 4 carbon atoms, such as for example, methoxymethyl, (d) an alkenyl group preferably containing 2 to 5 carbon atoms, (e) an aryl group especially phenyl which can be optionally substituted with one or more, such as 1 to 3, alkyl or halo groups, for example methyl and chloro, (f) an aralkyl group especially benzyl or phenethyl optionally substituted in the phenyl ring with one or more, such as 1 to 3, alkyl or halo groups, for example methyl and chloro, and (g) a phenoxyalkyl group especially phenoxymethyl, 1-phenoxyethyl or 2-phenoxyethyl, optionally substituted in the phenyl ring with one or more, such as 1 to 3, alkyl or halo groups, for example methyl and chloro. It is preferred that $R^5$ is an alkyl, an alkoxyalkyl, an aryl, an aralkyl or a phenoxyalkyl group, the alkyl group being most preferred of all.

The groups $R^3$ and $R^4$ can be the same or different and are selected from hydrogen and alkyl groups which contain, for example, from 1 to 4 carbon atoms, such as for example methyl.

A preferred group of compounds for use in the present invention is one of the following formula

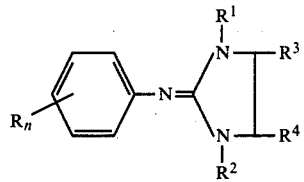
II in which n is 0 to 3, R is halo or alkyl, $R^1$ and $R^2$ are each hydrogen, alkyl, alkenyl or acyl, and $R^3$ and $R^4$ are each hydrogen or alkyl; or an acid addition salt thereof. Further preferred compounds are those in which (a) $R^3$ and $R^4$ are hydrogen, (b) n is 1 to 3, (c) R is halo or (d) $R^1$ is hydrogen or acyl of the formula $R^5CO$ and $R^2$ is acyl of the formula $R^5CO$, $R^5$ being alkyl of 1 to 10 carbon atoms. Thus especially desirable compounds for use in the invention are those of the following formula

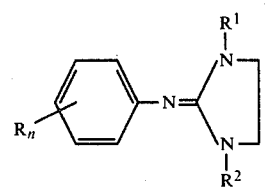

in which n is 1 to 3, R is halo, $R^1$ is hydrogen or acyl of the formula $R^5CO$ and $R^2$ is acyl of the formula $R^5CO$, $R^5$ being alkyl of 1 to 10 carbon atoms. These acylated derivatives possess superior activity to the non-acylated compounds. Of this group of compounds the most preferred are those in which $R^1$ is hydrogen.

A specific group of compounds for use in the invention has the following structure

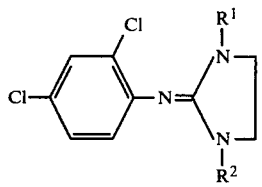

in which $R^1$ and $R^2$ are each hydrogen, acetyl or propionyl. One example of such compounds is 1-propionyl-2-(2,4-dichlorophenylimino)imidazolidine which is of great versatility in its uses.

In most circumstances it is satisfactory to employ the free base of formula I but, if desired, the active ingredient can be in the form of an acid addition salt, in which case the acid anion is one that is physiologically acceptable to the host animal, and when reference below is made to a compound of formula I or II it is meant to include acid addition salts. Convenient salts are those derived from both inorganic and organic acids, such as for example, hydrochloric, hydrobromic, hydriodic, sulphuric, nitric, phosphoric, sulphamic, acetic, trichloroacetic, benzenesulphonic, p-toluenesulphonic and picric acids.

Some of the compounds described above are novel, notably those of the following formula

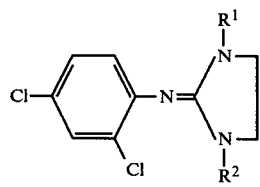

III in which $R^1$ is hydrogen and $R^2$ is $R^5CO$, $R^5$ being alkyl of 1 or 3 to 10 carbon atoms. These compounds are included as part of the invention, as indeed, are all of the specific examples of novel compounds in Examples 2 to 7 which follow.

A number of methods can be used to prepare the active compounds of formula I one of which comprises reacting an isothiouronium salt of the following formula

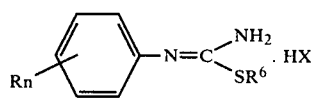

IV in which X can be for example iodine, with a diamine of the formula $HR^1NCHR^3CHR^4NHR^2$, in which n, R, $R^3$, $R^4$ have the meanings assigned them above, $R^1$ and $R^2$ are hydrogen, alkyl alkenyl or alkynyl, and $R^6$ is an alkyl group containing 1 to 4 carbon atoms for example methyl or ethyl, in the optional presence of a solvent such as methoanol, and at a temperature preferably within the range 50° to 200° C. Compounds of formula IV can be prepared by a route that comprises reacting a compound of the formula

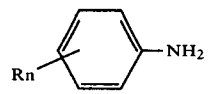

with benzoyl chloride and ammonium thiocyanate, then hydrolysing the product of this reaction with alkali, followed by treatment with alkyl halide.

A second method of preparation comprises reacting a chloroformimidoyl chloride of the formula

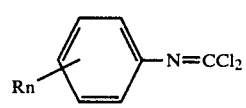

V with a diamine of the formula $R^1NHCHR^3CHR^4NHR^2$, preferably in the presence of a solvent such as for example other or benzene at a temperature of for example 0° to 25° C. In their turn, compounds of formula V can be prepared by reacting a mixture of sulphuryl chloride and thionyl chloride with a compound of the formula

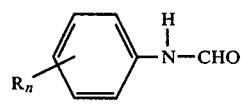

A third method of preparation comprises reacting a monoacylated pyrrolidone of the formula

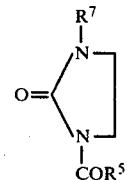

in which $R^5$ has the meaning assigned to it above and $R^7$ is alkyl, or alkenyl or alkynyl, with an arylamine of the formula

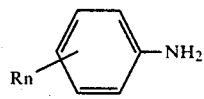

in the presence of for example phosphoryl chloride, at a temperature of from 50° to 70° C., followed by hydrolysis or reaction with a primary alcohol.

A further method for preparing compounds in which one or both $R^1$ and $R^2$ are alkyl or acyl, comprises reacting a compound of the formula

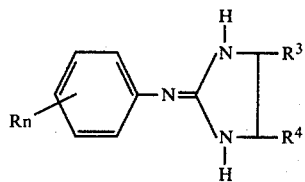

prepared, for example, in a manner such as described above, with the appropriate alkylating or acylating agent, for example methyl iodide, dimethyl sulphate, benzoyl chloride, acetyl chloride or acetic anhydride. This method can be modified somewhat in the case of mono-substituted compounds by first preparing a sodio-derivative, followed by reaction with the appropriate alkylating or acylating agent. Alternatively, acylated compounds can be prepared by the ommission of the final hydrolysis or alcoholysis step in the third method described above.

Another aspect of the invention is a method for controlling pests harmful to domestic animals, which comprises applying to the locus of the pest a compound of the following formula

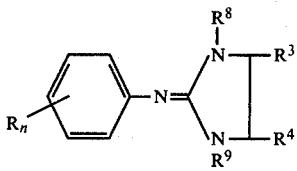

VI in which n is 0 to 5, R is halo, alkyl, trihaloalkyl, cyano, alkoxy or alkoxycarbonyl, $R^8$ and $R^9$ may be the same or different and one is the group

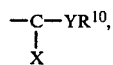

and the other is hydrogen or the group

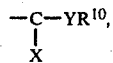

wherein X and Y may be the same or different and are oxygen or sulphur and $R^{10}$ is alkyl, substituted alkyl, cycloalkyl, alkenyl, substituted alkenyl alkynyl, substituted alkynyl, aryl or heteroaryl, and $R^3$ and $R^4$ are each hydrogen or alkyl; or an acid addition salt thereof. The term "locus" is used to imply that the active compounds can be applied to the pest itself or to the habitat of the pest. For example it is sometimes convenient to spray the quarters in which an animal is kept in order to eliminate the pest from the animal's surroundings. More usually the animal is treated by external application of the active compound either as a precaution against pest attack or in order to combat an infestation of pests.

Many of the compounds of the present invention are novel. Thus according to a further aspect of the invention there is provided compounds of formula VI in which the R groups are defined above with the proviso that when $R^9$, $R^3$ and $R^4$ are hydrogen and n is 2 then both R groups are not 2,6-dichloro.

It is known that imidazolidine compounds of the type VI, above, in which $R^1$ or $R^2$ is hydrogen may exhibit tautomerism between the iminoimidazolidine form (formula VI) and its aminoimidazoline tautomer. For convenience throughout this specification the compounds are referred to as iminoimidazolidines.

In formula VI, n can be 0 to 5 more usually 0 to 3. There is preferably at least one substituent and n is often 2. If n is more than one, the values of R need not be identical so that there can be mixed substituents on the phenyl ring.

In formula VI, when R is halo it can be iodo, chloro, fluoro or bromo and is preferably chloro or bromo. When it is alkyl R is preferably a group containing from 1 to 4 carbon atoms, such as for example methyl, ethyl, propyl, or butyl, especially methyl. In the case when R is trihaloalkyl it is preferably trifluoromethyl and when R is alkoxy the substituent is preferably one containing 1 to 4 carbon atoms, especially methoxy. When R is alkoxycarbonyl the substituent preferably contains 2 or 3 carbon atoms and is methoxycarbonyl or ethoxycarbonyl. In an especially preferred instance there are two substituents on the phenyl ring which are in the 2- and 4-positions, and particularly preferred are compounds having chlorine atoms in these positions. In formula VI, it is generally preferred that one of the groups $R^1$ and $R^2$ is hydrogen. When $R^{10}$ is alkyl, it is preferably lower alkyl of 1 to 4 carbon atoms and especially methyl. Examples of substituted alkyl groups included substituted $C_{1-4}$ alkyl, especially substituted methyl. Substituents may be halo e.g. fluoro, aryl, e.g. phenyl, alkoxy e.g. $C_{1-4}$ alkoxy, aryloxy e.g. phenoxy, the phenyl of which may be substituted by one or more groups such as alkyl, e.g. $C_{1-4}$ alkyl or halo groups. Examples of preferred substituted alkyl groups include trifluoromethyl, benzyl and methoxymethyl. When $R^{10}$ is cycloalkyl this is generally one containing 3 to 8 carbon atoms e.g. cyclohexyl. When $R^{10}$ is alkenyl this is generally $C_{2-5}$ alkenyl e.g. allyl. This may be substituted by for example halo or aryl to give groups such as chloroallyl, styryl and cinnamyl. When $R^{10}$ is alkynyl this is generally $C_{2-5}$ alkynyl e.g. prop-2-ynyl. This may be substituted by for example halo and aryl to give groups such as 1-chloroprop-2-ynyl. Examples of aryl groups include phenyl and phenyl substituted with one or more groups such as halo or alkyl e.g. $C_{1-4}$ alkyl and fused aryl groups. By the term heteroaryl is meant an aromatic heterocyclic group such as pyridyl, furyl, thienyl, benzothiazolyl and pyrrolyl which groups may be substituted by one or more groups such as alkyl, e.g. $C_{1-4}$ alkyl, and halo.

The groups $R^3$ and $R^4$ can be the same or different and are selected from hydrogen and alkyl groups which contain, for example, from 1 to 4 carbon atoms, such as for example methyl. Preferably both are hydrogen.

A specific group of compounds for use in the invention are those of formula VII.

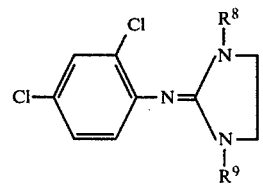

VII in which one of $R^1$ and $R^2$ is hydrogen and the other is $C_{1-4}$ alkoxycarbonyl. One example of such compounds is 2-(2,4-dichlorophenylimino)-1-methoxycarbonyl-imidazolidine.

In most circumstances it is satisfactory to employ the free base of formula VI but, if desired, the active ingredient can be in the form of an acid addition salt, in which case the acid anion is one that is physiologically acceptable to the host animal, and when reference below is made to a compound of formula VI or VII it is meant to include acid addition salts. The compounds of the invention generally have greater chemical stability in aqueous media than analogous compounds in which Y is absent. Convenient salts are those derived from both inorganic and organic acids, such as for example, hydrochloric, hydrobromic, hydriodic, sulphuric, nitric, phosphoric, sulphamic, acetic, trichloroacetic, benzenesulphonic, p-toluenesulphonic and picric acids.

A number of methods can be used to prepare the novel active compounds of formula VII one of which comprises reacting pyrrolidone of the formula

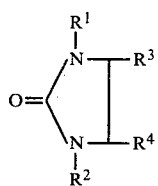

with an arylamine of the formula

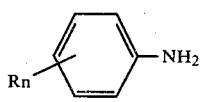

in the presence of for example phosphoryl chloride, at a temperature of for example 40° to 80° C.

A second method for preparing compounds of the invention comprises reacting a compound of the formula VIII

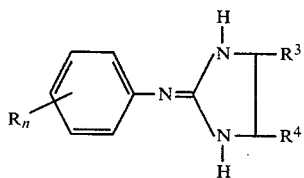

with a compound of formula

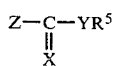

where Z is a leaving group such as halogen. This method can be modified somewhat in the case where one of $R_1$ and $R_2$ is to be hydrogen by first preparing a sodio-derivative. Where compounds of formula VIII are novel they may be prepared as described previously.

When animals are attacked by parasites there can be great economic loss and, as mentioned above, the method of the invention is especially applicable to animal livestock and to the control of insect or acarid ectoparasites which attach themselves to the external parts of the animal at some stage during their life cycle (the acarid ectoparasites are arthropods of the order Acarina). For example ticks, mites, keds, lice and flies are amongst the pests which are serious problem in the rearing of cattle, pigs and sheep. We have found that the method of the invention is particularly applicable to the control of acarid ectoparasites which attack livestock, especially cattle and pigs. Accordingly the invention includes a method for controlling acarid ectoparasites harmful to livestock which comprises applying to the locus of the pest a compound of formula I or VII. It is often convenient to apply the active compound directly to the external parts of the animal and so a further aspect of the invention is a method for controlling ectoparasites which comprises externally applying to livestock a compound of the formula II or VII. This method is especially effective in the treatment of cattle infested with ticks of the family Ixodidae, for example, the species *Boophilus microplus, Boophilus decoloratus, Rhipicephalus evertsi, Rhipicephalus appendiculatus, Amblyomma hebraeum* and *Hyalomma rufipes*. Thus the invention includes a method for protecting cattle from cattle tick which comprises treating the cattle externally with a compound of formula II or VII.

Techniques for externally treating livestock are well-known in the art, the most commonly used being the spray, dip and pour-on techniques. The animal can be sprayed with a composition containing the active ingredient by means of, for instance a hand spray or spray race. In essence the dip method of treatment entails passing the animal through an aqueous medium containing the active compound in a conventional dip apparatus such as a cattle dip. As an alternative, the pour-on technique involves the use of smaller quantities of liquid for application along the back of an animal.

The dosage of active ingredient depends on the nature of the infestation and on the host animal. When it is the sole pesticide employed, an amount within the range of from 0.1 to 100 mg, more especially from 0.5 to 75 mg, per kilogram body weight of the host is often appropriate. It is often convenient to employ a spray or dip wash with a concentration of from 0.001 to 1.0 percent, more especially from 0.005 to 0.5 percent by weight of active ingredient. In the case of a pour-on composition for application to cattle the amount applied to the animal can vary, for instance, within the limits of from 0.1 to 10 gm, more especially from 0.5 to 5 gm, per beast.

As indicated above, a compound of formula I or VI is preferably applied as one of the many well-known formulations employed in animal husbandry. The invention includes such pesticidal compositions for application to domestic animals which comprise a compound of formula I, or VII optionally together with diluent or carrier, in the form of for example a solution, an aqueous dispersion, an aqueous emulsion, a dusting powder, a dispersible powder, a fumigant, an emulsifiable concentrate or a dispersible concentrate.

In the case of animal livestock the compound of formula I or VI can, in many instances, be employed as a spray or dip. The material is often prepared by diluting a dispersible powder or emulsifiable concentrate with water, and as a particular aspect of the invention there is included a cattle or sheep dip which comprises an active ingredient of formula I or VI in association with a surfactant, the nature and proportion of the ingredients being such that, on dilution with an appropriate quantity of water, stable aqueous compositions are produced that are suitable for the treatment of cattle, or sheep by the conventional procedures of dipping and spraying.

A dispersible powder comprises the active ingredient in finely divided form in association with a dispersing agent, the concentration of active ingredient being from, for example, 5 to 95 percent by weight of the composition. Additional materials such as for example, a suspending or antifoaming agents may be employed and a finely divided inert solid diluent such as kaolin, precipitated silica, talc or diatomaceous earth is generally incorporated in the dispersible powder.

An emulsifiable concentrate comprises an active ingredient together with an emulsifying agent and optionally dissolved in the medium of a water-immiscible solvent, the concentration of active ingredient being from, for example, 5 to 95 percent by weight of the composition.

Surfactants such as the dispersible and emulsifying agents employed in the dispersible powder and emulsifiable concentrate can be any of those commonly used, which include for example, anionic, nonionic and cationic compounds. Anionic compounds include for example a carboxylate such as a metal carboxylate of a long chain fatty acid; an N-acylsarcosinate; a sulphonate such as an alkylbenzenesulphonate or a petroleum sulphonate; a sulphate such as a sulphated alcohol, a sulphated natural fat or oil; or a phosphate ester such as an alkyl orthophosphate or an allyl polyphosphate. Nonionic compounds include for example an ethoxylated alkylphenol such as a nonly phenoxypoly(ethyleneoxy)ethanol; an ethoxylated aliphatic alcohol such as an alkylpoly(ethyleneoxy)ethanol; or a carboxylic ester solublised with a polyol or polyoxyethylene. Examples of a cationic agent include, for instance, an aliphatic mono-, di-, or polyamine as an acetate, naphthenate or oleate; an oxygen containing amine such as amine oxide or polyoxyethylene alkylamine; an amide-linked amine prepared by the condensation of a carboxylic acid with a di- or polyamine; or a quaternary ammonium salt.

When in the form of a pour-on composition, the active ingredient can be suspended or dissolved in a variety of media including, for example, an aqueous medium, an organic solvent or an oil vehicle. When water is used as the medium it can be convenient to employ a flowable composition of finely divided particles of a solid active ingredient suspended in the aqueous medium. Alternatively it is often convenient to use an oil medium and suitable materials include oils of animal, vegetable or mineral origin, for example, sunflower seed oil, maize oil, polyethylene glycol or liquid paraffin.

As stated above the invention includes cattle or sheep dips, sprays, dispersible powders, emulsifiable concentrate, and pour-on compositions and in addition the following specific compositions: (a) A cattle or sheep dip comprising 1-propionyl-2-(2,4-dichlorophenylimino)imidazolidine in association with a surfactant and optionally in addition a diluent or carrier, the nature and proportion of the ingredients being such that, on dilution with an appropriate quantity of water, a stable aqueous composition is produced that is suitable for the treatment of cattle or sheep. (b) A pesticidal composition in the form of a dispersible powder comprising 1-propionyl-2-(2,4-dichlorophenylimino)-imidazolidine in finely divided form in association with a dispersing agent, the concentration of the active ingredient being from 5 to 95 percent by weight of the powder. (c) A pesticidal pour-on composition comprising 1-propionyl-2-(2,4-dichlorophenylimino)imidazolidine in the form of a finely divided dispersion of particles having an average diameter of from 0.1 to 20 microns in an aqueous medium, the active ingredient being present to the extent of from 2 to 60 percent by weight.

(d) A pesticidal pour-on composition comprising 1-propionyl-2-(2,4-dichlorophenylimino)imidazolidine dissolved in a medium comprising a pharmacologically acceptable oil, the active ingredient being present to the extent of from 2 to 60 percent by weight.

Similar formulations to (a) to (d) comprising an active ingredient of formula III or VII or a novel compound as described in any of Examples 2 to 7 or 15 or 16, are included in the invention.

In addition to its relevance in animal husbandry the method of the invention is of practical application in the treatment of cats and dogs which are subject to infestation by pests, and accordingly the invention comprises a method for controlling an infestation of pests on a cat or dog which comprises applying to the pests a compound of formula I or VI above. Application of the active compound can be by any of the methods known for grooming pets, in order to control a wide range of pests, especially mites. Particularly convenient ways of applying the active compound are, in this instance, by means of a wash prepared from a dispersible powder or a dusting powder. The latter comprises a compound of formula I or VI intimately mixed and ground with a solid pulverulent diluent, for example kaolin. An example of a pesticidal dusting powder suitable for treating a cat or dog is one that comprises 1-propionyl-2-(2,4-dichlorophenylimino)imidazolidine intimately mixed with a solid pulverulent diluent, the active ingredient being present to the extent of, for example, from 1 to 50 percent by weight of the dusting powder.

A compound of formula I or VI may be employed in combination with other pesticides for controlling ectoparasites, if desired. Such additional pesticides include, for example, an organophosphorus compound such as tetrachlorvinphos, oxinothiophos, fenitrothion, phosalone, dioxathion, chlorfenvinphos, coumaphos, bromophos-ethyl or chlorpyrifos; a carbamate such as carbaryl or promecarb; a bridged diphenyl compound such as tedion, tetrasul, chlorbenside or DDT; a chlorinated hydrocarbon such as benzene hexachloride or toxaphene; clenpyrin; chlormethiuron; nimidane; amitraz; or a synthetic pyrethroid such as NRDC 143.

The invention is illustrated by the following Examples

EXAMPLE 1

A solution of 46 g 2-(2,4-dichlorophenylimino)imidazolidine and 28.6 g propionic anhydride in one liter of dry toluene was allowed to stand at room temperature for 24 hours. The solution was washed with aqueous sodium bicarbonate solution and then water, and dried over magnesium sulphate. Evaporation gave the required propionyl derivative which was recrystallised from propan-2-ol to give the pure material, 1-propionyl-2-(2,4-dichlorophenylimino)imidazolidine, melting point 126°–128° C.

The 2-(2,4-dichlorophenylimino)imidazolidine employed in the above rreaction was prepared as follows.

To a stirred solution of 167 g ammonium thiocyanate in one liter of acetone was rapidly added 282 g benzoyl chloride. The mixture was refluxed for five minutes and then a solution of 324 g 2,4-dichloroaniline in one liter of acetone was added gradually so as to maintain gentle reflux. When the addition was completed, the mixture was stirred and refluxed for thirty minutes before cooling and adding to iced water.

The solid benzoyl derivative was filtered off, washed with water and then suspended in four liters of 10 percent aqueous sodium hydroxide solution. The mixture was stirred and heated on the steam bath for one hour, treated with charcoal and filtered whilst hot. The cooled filtrate was acidified with hydrochloric acid and then made just alkaline with ammonium hydroxide. The resulting white solid was filtered off and dried. Recrystallisation with charcoal from ethanol gave the pure thiourea, 2,4-dichlorophenylthiourea, melting point 157°–159° C.

A mixture of 193.7 g of this thiourea, 88 ml water and 111 g dimethyl sulphate was stirred and warmed with a free flame until reaction started. The solution was refluxed for one hour and then evaporated. Residual traces of dimethyl sulphate were codistilled with water and then ethanol.

The residual oily liquid was dissolved in one liter of methanol and 175 ml of ethylene diamine was added dropwise with stirring. The mixture was refluxed for twenty hours, filtered, and the filtrate evaporated. The residual syrup was added to iced water and basified with aqueous sodium hydroxide solution. The resulting white solid was filtered off and dried. Recrystallisation with charcoal from ethyl acetate gave 2-(2,4-dichlorophenylimino)imidazolidine, melting point 151°–152° C.

1-Propionyl-2-(2,4-dichlorophenylimino)imidazolidine was reacted with the appropriate acid to give the following salts:

1-propionyl-2-(2,4-dichlorophenylimino)imidazolidine picrate, melting point 232°–233° C.

1-propionyl-2-(2,4-dichlorophenylimino)imidazolidine hydrochloride, melting point 190°–192° C.

EXAMPLE 2

A mixture of 11.5 g 2-(2,4-dichlorophenylimino)imidazolidine 1.7 g sodium hydride (80 percent dispersion in oil) and 80 ml dry tetrahydrofuran was stirred and refluxed for one and a half hours, and a solution of 5.9 g isobutyryl chloride in 20 ml dry tetrahydrofuran was then added dropwise. The mixture was stirred and refluxed for five hours and then cooled and poured into iced water to give a solid which was dried over phosphorus pentoxide. Recrystallisation with charcoal from ethanol gave the novel compound 1-isobutyryl-2-(2,4-dichlorophenylimino)imidazolidine, melting point 147°–148° C.

The iminoimidazolidine compound employed in the above reaction was prepared according to the method described in Example 1.

The following novel compounds were prepared by a similar method. Where the compound isolated was a syrup and could not therefore be characterised by means of a melting point or boiling point the $R_F$ value is quoted, as obtained by thin layer chromatography using Merck Kieselgel 60 PF$_{254}$. The spots on the chromatograph were located by means of ultra violet radiation and in each instance the solvent employed is quoted in brackets. The structure was confirmed by elemental analysis.

1-butyryl-2-(2,4-dichlorophenylimino)imidazolidine, m.p. 141°–142° C.

1-benzoyl-2-(2,4-dichlorophenylimino)imidazolidine, m.p. 169°–170° C.

1-valeryl-2-(2,4-dichlorophenylimino)imidazolidine, m.p. 111°–112° C.

1-hexanoyl-2-(2,4-dichlorophenylimino)imidazolidine, m.p. 103°–104° C.

1-allyl-2-(2,4-dichlorophenylimino)imidazolidine, m.p. 72°–73° C.

1-pivaloyl-2-(2,4-dichlorophenylimino)imidazolidine, m.p. 129°–130° C.

1-methyl-2-(2)-4-dichlorophenylimino)-3-propionylimidazolidine, a syrup $R_F$ 0.6 (ethyl acetate).

1-(but-2-enyl)-2-(2,4-dichlorophenylimino)imidazolidine, a syrup, $R_F$ 0.4 (9:1 toluene and industrial methylated spirit)

1-(prop-2-ynyl)-2-(2,4-dichlorophenylimino)imidazolidine, m.p. 59°–62° C.

1-nonyl-2-(2,4-dichlorophenylimino)imidazolidine, a syrup, $R_F$ 0.5 (ethyl acetate).

1-(DL-2-methylbutyryl)-2-(2,4-dichlorophenylimino)imidazolidine, m.p. 107°–109° C.

1-heptanoyl-2-(2,4-dichlorophenylimino)imidazolidine, m.p. 119°–121° C.

1-p-chlorobenzoyl-2-(2,4-dichlorophenylimino)imidazolidine, m.p. 154°–155° C.

1-m-chlorobenzoyl-2-(2,4-dichlorophenylimino)imidazolidine, m.p. 150°–152° C.

1-o-chlorobenzoyl-2-(2,4-dichlorophenylimino)imidazolidine, m.p. 156°–157° C.

1-octanoyl-2-(2,4-dichlorophenylimino)imidazolidine, m.p. 95°–97° C.

1-nonanoyl-2-(2,4-dichlorophenylimino)imidazolidine, m.p. 96°–98° C.

1-cyclopropanecarbonyl-2-(2,4-dichlorophenylimino)imidazolidine, m.p. 148°–149° C.

1-cyclobutanecarbonyl-2-(2,4-dichlorophenylimino)imidazolidine, m.p. 136°–137° C.

1-cyclopentanecarbonyl-2-(2,4-dichlorophenylimino)imidazolidine, m.p. 130°–131° C.

1-cyclohexanecarbonyl-2-(2,4-dichlorophenylimino)imidazolidine, m.p. 135°–136° C.

1-(3,4-dichlorobenzoyl)-2-(2,4-dichlorophenylimino)imidazolidine m.p. 175°–176° C.

1-ethoxycarbonyl-2-(2,4-dichlorophenylimino)imidazolidine, m.p. 138°–139° C.

1-(2-phenoxypropionyl)-2-(2,4-dichlorophenylimino)imidazolidine, m.p. 147°–148° C.

1-p-bromobenzoyl-2-(2,4-dichlorophenylimino)imidazolidine, m.p. 177°–179° C.

1-hexyl-2-(2,4-dichlorophenylimino)imidazolidine, a syrup, $R_F$ 0.5 (ethyl acetate)

1-(2,5-dichlorobenzoyl)-2-(2,4-dichlorophenylimino)imidazolidine m.p. 144°–146° C.

1-p-nitrobenzoyl-2-(2,4-dichlorophenylimino)imidazolidine, m.p. 205°–206° C.

1-phenylacetyl-2-(2,4-dichlorophenylimino)imidazolidine, m.p. 170°–173° C.

1-pivaloylmethyl-2-(2,4-dichlorophenylimino)imidazolidine, a syrup, $R_F$ 0.4 (ethyl acetate)

1-(pent-4-enoyl)-2-(2,4-dichlorophenylimino)imidazolidine, m.p. 97°–97.5° C.

1-(3-methylbut-2-enyl)-2-(2,4-dichlorophenylimino)imidazolidine, m.p. 55°–56° C.

EXAMPLE 3

A solution of 12.1 g N-2,4-dichlorophenylchloroformimidoyl chloride in 50 ml dry ether was added dropwise with stirring to 18.5 g N-methylethylene diamine in 75 ml dry ether at 10° to 15° C. Heat was evolved and an oily precipitate formed. After stirring at room temperature for one and a half hours, the mixture was poured into iced water. The mixture was extracted with ether and the combined ethereal extracts were washed with water and then dried over magnesium sulphate. Evaporation in vacuo gave a clear syrup which was dissolved in ether and ethereal hydrogen chloride was added, and the precipitated hydrochloride was dried over phosphorus pentoxide. A portion of the hydrochloride was recrystallised from methanol/ether mixture to give a product having a melting point 229°–231° C.

The remainder of the hydrochloride was converted to the free base by dissolving it in water, treating the solution with charcoal and basifying with sodium hydroxide. The free base was extracted with dichloromethane and washed with water and then dried over magnesium sulphate. Evaporation gave the novel compound 1-methyl-2-(2,4-dichlorophenylimino)imidazolidine, as a colourless syrup. When the compound was subjected to thin layer chromatography on Merck Kieselgel 60PF$_{254}$, employing ethyl acetate as solvent and observed by means of ultra violet radiation, it was found to have an R$_F$ value of 0.3. A satisfactory elemental analysis was obtained.

The N-2,4-dichlorophenylchloroformimidoyl chloride employed in the above method was prepared as follows. To a mixture of 67.5 g sulphuryl chloride and 150 ml thionyl chloride maintained at 15° to 20° C., was added in portions 95.0 g 2,4-dichloroformanilide. When the addition was completed the suspension was stirred at room temperature for two hours, then gradually warmed to 80° C. over a period of two and a half hours and finally heated at 80° C. for half and hour. The mixture was filtered and the filtrate was evaporated in vacuo from a water bath at 50° C. Distillation of the residue gave a yellow oil, boiling point 116°–119° C./5 mm.

The following novel compound was made by a similar method, 2-(4-chloro-2-trifluoromethylphenylimino)imidazolidine, m.p. 185°–187° C.

EXAMPLE 4

A solution of 43.5 g of 2,3,4-trichlorophenylthiourea and 35.5 g methyl iodide in 170 ml methanol was refluxed gently for one and a half hours. The solution was evaporated and the residual methyl iodide was codistilled by addition and then evaporation of more methanol. The resulting solid was refluxed overnight with 34 ml ethylenediamine and 170 ml methanol. The solution was evaporated to give a solid which was suspended in iced water, filtered off and dried over phosphorus pentoxide to give 2-(2,3,4-trichlorophenylimino)imidazolidine. This novel compound, recrystallised from ethyl acetate, had a melting point of 161° C.

The 2,3,4-trichlorophenylthiourea employed in the reaction above was prepared as follows. To a stirred solution of 42.0 g ammonium thiocyanate in 200 ml acetone at room temperature was added rapidly from a dropping funnel 70.3 g benzoyl chloride. The mixture was refluxed for five minutes and then a solution of 98.3 g 2,3,4-trichloroaniline in 150 ml acetone was added gradually so as to maintain gentle reflux. A thick precipitate formed and it was necessary to add more acetone to facilitate stirring. The mixture was stirred and refluxed for thirty minutes and then poured into iced water. The benzoyl derivative was filtered off, washed with water, then suspended in 1 liter of 10 percent sodium hydroxide solution. The mixture was stirred and heated on the steambath for one hour, treated with charcoal and filtered whilst hot. It was acidified with concentrated hydrochloric acid and then made just alkaline with ammonium hydroxide solution. The solid was filtered off, dried and recrystallised with charcoal from propan-2-ol to give 2,3,4-trichlorophenylthiourea, melting point 185°–186° C.

The following novel compound was made by a similar method, 2-(4-chloro-2-ethylphenylimino)imidazolidine, melting point 115°–117° C.

EXAMPLE 5

A solution of 2.3 g 2-(2,4-dichlorophenylimino)imidazolidine and 1.1 g acetic anhydride in 50 ml dry benzene was allowed to stand at room temperature for three days. The white crystalline solid was filtered off and washed with benzene to give the novel compound 1-acetyl-2-(2,4-dichlorophenylimino)imidazolidine, melting point 168°–169° C.

The iminoimidazolidine compound employed in the above reaction was prepared according to the method described in Example 1.

The following novel compounds were made by a similar method.

1-propionyl-2-(2,4-dibromophenylimino)imidazolidine, m.p. 162°–163° C.

1-propionyl-2-(2-bromo-4-chlorophenylimino)imidazolidine, m.p. 151°–152° C.

1-propionyl-2-(4-bromo-2-chlorophenylimino)imidazolidine, m.p. 134°–135° C.

EXAMPLE 6

A mixture of 7 ml acetic anhydride and 2.3 g 2-(2,4-dichlorophenylimino)imidazolidine was heated on the steam bath for two hours, cooled and poured into iced water. The white solid was collected and dried over phosphorus pentoxide and then recrystallised from ethanol to give the novel compound, 1,3-diacetyl-2-(2,4-dichlorophenylimino)-imidazolidine, melting point 113°–115° C.

The iminoimidazolidine compound employed in the above reaction was prepared according to the method described in Example 1.

The following novel compound was prepared by a similar method, 1,3-dipropionyl-2-(2,4-dichlorophenylimino)imidazolidine m.p. 94°–95° C.

EXAMPLE 7

A solution of 6.9 g 2-(2,4-dichlorophenylimino)imidazolidine and 150 ml ethyl formate was refluxed gently on the steam bath for twenty minutes. The mixture was cooled and filtered to give a white solid. Recrystallisation from propan-2-ol gave the novel compound 1-formyl-2-(2,4-dichlorophenylimino)imidazolidine hydrate, melting point 168°–170° C.

The iminoimidazolidine compound employed in the above reaction was prepared according to the method described in Example 1.

EXAMPLE 8

This Example illustrates a flowable composition comprising 1-propionyl-2-(2,4-dichlorophenylimino)imidazolidine. The following ingredients were mixed together and ground in the wet state by means of a ball mill.

| | |
|---|---|
| 1-Propionyl-2-(2,4-dichlorophenylimino)imidazolidine | 50.0% w/v |
| Bentonite (colloidal hydrated aluminium silicate) | 4.0% w/v |
| Dyapol PT (a sulphonated condensate of urea, cresol and formaldehyde) | 5.0% w/v |
| Aerosol OT-B (a mixture of sodium dioctyl sulphosuccinate and sodium benzoate) | 0.1% w/v |
| Antifoam M30 (a silicone-based antifoam) | 0.1% w/v |
| Water | to 100.0% volume |

Such a flowable composition can be used as a pour-on or a suitable spray or cattle dip prepared by dilution of 2.5 liters of the composition in 2500 liters of water.

EXAMPLE 9

This Example illustrates dispersible powders prepared, for example, by mixing the following ingredients

| | |
|---|---|
| 1-Propionyl-2-(2,4-dichlorophenylimino)-imidazolidine | 50.0% w/w |
| Polyfon F (sodium lignosulphonate) | 10.0% w/w |
| Aerosol OT-B | 0.5% w/w |
| Colloidal silicic acid | 5.0% w/w |
| Kaolin | 34.5% w/w |

Similar dispersible powders were prepared substituting as active ingredient the following compounds,
  2-(2,4-dichlorophenylimino)imidazolidine
  2-(4-chloro-2-trifluorophenylimino)imidazolidine
  1,3-diacetyl-2-(2,4-dichlorophenylimino)imidazolidine
  1-acetyl-2-(2,4-dichlorophenylimino)imidazolidine
  1,3-dipropionyl-2-(2,4-dichlorophenylimino)imidazolidine
  1-benzoyl-2-(2,4-dichlorophenylimino)imidazolidine
  1-valeryl-2-(2,4-dichlorophenylimino)imidazolidine
  1-p-chlorobenzoyl-2-(2,4-dichlorophenylimino)imidazolidine
  1-propynyl-2-(2,4-dichlorophenylimino)imidazolidine

EXAMPLE 10

This Example illustrates emulsifiable concentrates prepared, for example, by mixing the following ingredients to produce a solution.

| | |
|---|---|
| 1-Methyl-2-(2,4-dichlorophenylimino)-imidazolidine | 10.0% w/v |
| Agrilan CA (calcium dodecyl benzene sulphonate with nonylphenol ethoxylates) | 5.0% w/v |
| Agrilan BA (calcium dodecyl benzene sulphonate with nonylphenol ethoxylates) | 5.0% w/v |
| Xylene | to 100.0% volume |

Similar emulsifiable concentrates were prepared substituting as active ingredient the following compounds
  1-methyl-2-(2,4-dichlorophenylimino)-3-propionylimidazolidine
  1-methylallyl-2-(2,4-dichlorophenylimino)imidazolidine
  1-nonyl-2-(2,4-dichlorophenylimino)imidazolidine

EXAMPLE 11

This Example illustrates the preparation of pour-on formulations. The following ingredients were mixed to provide a solution in convenient form for application to animals.

| | |
|---|---|
| 1-Methyl-2-(2,4-dichlorophenylimino) imidazolidine | 5.0% w/v |
| Xylene | 20.0% v/v |
| Liquid paraffin | 30.0% v/v |
| Maize oil | to 100.0% volume |

Similar pour-on formulations were prepared employing the active ingredients listed in Example 10.

EXAMPLE 12

The activity of compounds against the cattle tick, *Boophilus microplus*, was tested in the following way.

Two filter papers were each impregnated with 0.4 ml of acetone solution of the test compound. The acetone was allowed to evaporate and one of the filter papers was inserted into the inverted lid of a 5 cm petri dish. A cardboard washer was placed on top of the impregnated filter paper and approximately 50 seven-day old larvae of the Biarra strain of *Boophilus microplus* were placed within the space enclosed by the washer. The remaining impregnated filter paper was placed on top of the cardboard washer and held in place by inserting the base of the petri dish inside the lid and securing it by means of elastic bands. The whole was placed in a humidified incubator at 26° C. for 48 hours and then examined. At a concentration of 500 parts per million all of the compounds of formula I named in Examples 1 to 7 gave greater than 50 percent kill, as in addition did the following compounds:
  2-(2,3-dichlorophenylimino)imidazolidine
  2-(2,4,5-trichlorophenylimino)imidazolidine
  2-(2-methyl-4-chlorophenylimino)imidazolidine
  2-(2-chloro-4-methylphenylimino)imidazolidine
  2-(2-bromo-4-chlorophenylimino)imidazolidine
  2-(4-bromo-2-chlorophenylimino)imidazolidine
  2-(2,4-dibromophenylimino)imidazolidine
  2-(2-chloro-4-bromophenylimino)imidazolidine
  2-(2,4-dimethylphenylimino)imidazolidine
  2-(2,4,6-trichlorophenylimino)imidazolidine
  1-methoxymethyl-2-(2,4-dichlorophenylimino)imidazolidine.

EXAMPLE 13

In the following experiments calves were employed that had been given equal inocula of infective larvae of the cattle tick, *Boophilus microplus*, three times per week for three weeks up to the time of treatment. All parasitic stages, from larvae to gravid females, were thus present at the time of treatment.

The active ingredients were sprayed on the calves to run-off, the spray containing 0.05 percent active ingredient, which represents a dosage of approximately 4 gm per calf (weighing approximately 130 kilograms). The spray was applied by means of a mechanical hand spray.

An assessment of activity was made by counting the number of gravid female ticks shed by the treated animals and making a comparison with control animals that had not been treated with active ingredient. Both of the following compounds resulted in greater than 70 percent control 1-propionyl-2-(2,4-dichlorophenylimino)imidazolidine 1-acetyl-2-(2,4-dichlorophenylimino)imidazolidine.

EXAMPLE 14

The activity of 1-propionyl-2-(2,4-dichlorophenylimino)imidazolidine was tested against *Sarcoptes scabiei* the cause of sarcoptic mange in pigs.

A heavily infested piglet weighing approximately 35 kilograms was sprayed all over with 500 ml of an aqueous dispersion of the active compound at a concentration of 0.1 percent. The spraywash was applied by means of a mechanical hand spray and particular attention was paid to treating the insides of the ears.

A second spray treatment with 500 ml of the aqueous dispersion was applied eighteen days after the first treatment.

Ear scrapings were taken and examined microscopically at intervals after this treatment and it was found that the mange mite had been completely eliminated.

EXAMPLE 15

A mixture of 2-(2,4-dichlorophenylimino)imidazolidine (9.2 g.), sodium hydride (1.3 g. as 80% dispersion in oil) and tetrahydrofuran (65 ml.) was stirred and heated under reflux for 1 hour. The mixture was cooled and a solution of ethyl chloroformate (4.8 g.) in tetrahydrofuran (20 ml.) was added dropwise. The mixture was then stirred and heated under reflux for a further three hours. The mixture was cooled and then poured onto an ice-water mixture to give a solid which was dried over phosphorus pentoxide. Recrystallisation with charcoal from isopropanol gave 2-(2,4-dichlorophenylimino)-1-ethoxycarbonylimidazolidine, m.p. 138°–139° C.

EXAMPLE 16

In a similar manner to that described in Example 15 using the appropriate imidazolidine and chloroformate ester the following compounds were obtained.

2-(2,4-dichlorophenylimino)-1-methoxycarbonylimidazolidine m.p. 166°–167° C.
2-(2,4-dichlorophenylimino)-1-propoxycarbonylimidazolidine m.p. 122°–123° C.
2-(2,4-dichlorophenylimino)-1-isopropoxycarbonylimidazolidine m.p. 131°–133° C.
2-(2-bromo-4-chlorophenylimino)-1-methoxycarbonylimidazolidine m.p. 194°–195° C.
2-(4-chloro-2-methylphenylimino)-1-methoxycarbonylimidazolidine m.p. 158°–159° C.
1-butoxycarbonyl-2-(2,4-dichlorophenylimino)imidazolidine m.p. 108°–109° C.
2-(2,4-dimethylphenylimino)-1-methoxycarbonylimidazolidine m.p. 174°–176° C.
2-(2,4 -dichlorophenylimino)-1-isobutyloxycarbonylimidazolidine m.p. 119°–120° C.
2-(2,4-dichlorophenylimino)-1-pentyloxycarbonylimidazolidine m.p. 92°–93° C.
2-(2,4-dichlorophenylimino)-1-ethylthiocarbonylimidazolidine m.p. 137°–138° C.
1-benzyloxycarbonyl-2-(2,4-dichlorophenylimino)imidazolidine m.p. 133°–134° C.
1-cyclopentyloxycarbonyl-2-(2,4-dichlorophenylimino)imidazolidine m.p. 138°–139° C.
1-cyclohexyloxycarbonyl-2-(2,4-dichlorophenylimino)imidazolidine m.p. 148°–150° C.
2-(2,4-dichlorophenylimino)-1-(1-naphthyloxycarbonyl)imidazolidine m.p. 201°–203° C.
2-(4-chloro-2-trifluoromethylphenylimino)-1-methoxycarbonylimidazolidine m.p. 153°–154° C.
2-(4-bromo-2-chlorphenylimino)-1-methoxycarbonylimidazolidine m.p. 177°–178° C.
2-(2,4-dibromophenylimino)-1-methoxycarbonylimidazolidine m.p. 205°–206° C.
2-(2,4-dibromophenylimino)-1,3-di(methoxycarbonyl)imidazolidine m.p. 113°–114° C.

The starting material for the last compound of this Example was the product of the first compound of the Example and the starting material for compound 15 of this Example was the last mentioned product of Example 3.

EXAMPLE 17

The products of Examples 15 and 16 were tested for their activity against cattle tick as described in Example 12. At a concentration of 500 ppm all the products gave greater than 50% kill.

We claim:

1. The method for combating an infestation of insect or acarid ectoparasites harmful to domestic animals which comprises contacting the ectoparasite with a concentration of from 0.001 to 1.0 percent by weight of a compound of the formula

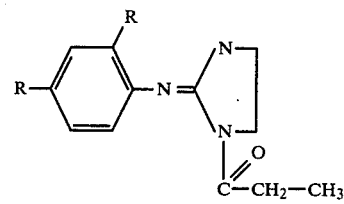

in which R is selected from the group consisting of halo, alkyl of 1 to 4 carbon atoms, inclusive; trifluoromethyl; cyano; alkoxy of 1 to 4 carbon atoms, inclusive; methoxycarbonyl, and ethoxycarbonyl; and acid addition salts thereof.

2. The method for combating an infestation of insect or acarid ectoparasites harmful to domestic animals according to claim 1 wherein "R" substituents are halogen or alkyl and acid addition salts thereof.

3. The method according to claim 2 for combating ectoparasites which comprises externally applying the compound to livestock.

4. The method according to claim 3 for combating ectoparasites which comprises externally applying to livestock a compound wherein both "R's" are halogen.

5. The method according to claim 4 for combating ectoparasites which comprises externally applying to livestock a compound wherein both "R's" are chlorine.

6. The method according to claim 3 for combating the cattle tick which comprises externally applying to livestock the compound in a concentration of 500 parts per million.

7. A method according to claim 4 in which the livestock are cattle or pigs.

8. A method according to claim 7 in which the livestock are treated with an amount of active compound within the range of from 0.5 to 75 mg per kilogram body weight.

9. The method according to claim 2 for combating an infestation of ectoparasites on a cat or dog.

10. A cattle or sheep dip composition suitable for combating ectoparasites comprising an ectoparasiticidal amount of 1-propionyl-2-(2,4-dichlorophenylamino)-imidazolidine in association with a surfactant, the nature and proportion of the ingredients being such that, on dilution with an appropriate quantity of water, a stable aqueous composition is produced that is suitable for the treatment of cattle or sheep.

11. An ectoparaiticidal composition in the form of a dispersible powder comprising 1-propionyl-2-(2,4 dichlorophenylimino)imidazolidine in finely divided form in association with a dispersing agent, the concentration of the active ingredient being from 5 to 95 percent by weight of the powder.

12. An ectoparaiticidal pour-on composition comprising 1-propionyl-2-(2,4-dichlorophenylimino)-imidazolidine in the form of a finely divided dispersion of particles having an average diameter of from 0.1 to 20 microns in an aqueous medium the active ingredient being present to the extent of 2 to 60 percent by weight.

13. An ectoparaiticidal pour-on composition comprising 1-propionyl-2-(2,4-dichlorophenylimino)imidazolidine dissolved in a medium comprising a pharmacologically acceptable oil, the active ingredient being present to the extent of from 2 to 60 percent by weight.

14. An ectoparaiticidal dusting powder suitable for treating a cat or dog comprising 1-propionyl-2-(2,4-dichlorophenylimino)imidazolidine intimately mixed with a solid pulverulent diluent, the active ingredient being present to the extent of from 1 to 50 percent by weight of the dusting powder.

15. The method according to claim 3 in which the livestock are treated with an amount of active compound within the range of from 0.5 to 75 mg per kilogram body weight.

* * * * *